(12) United States Patent
Stanley et al.

(10) Patent No.: US 11,307,193 B1
(45) Date of Patent: Apr. 19, 2022

(54) GLUCOSE TESTING DEVICE WITH TEST STRIP DISPENSER

(71) Applicants: Joshua Stanley, Turlock, CA (US); Richard Stanley, Turlock, CA (US); Tony Golobe, Turlock, CA (US); Shawn Peterson, Turlock, CA (US)

(72) Inventors: Joshua Stanley, Turlock, CA (US); Richard Stanley, Turlock, CA (US); Tony Golobe, Turlock, CA (US); Shawn Peterson, Turlock, CA (US)

( * ) Notice: Subject to any disclaimer, the term of this patent is extended or adjusted under 35 U.S.C. 154(b) by 344 days.

(21) Appl. No.: 16/708,538

(22) Filed: Dec. 10, 2019

(51) Int. Cl.
*G01N 33/487* (2006.01)
*G01N 33/66* (2006.01)

(52) U.S. Cl.
CPC ....... *G01N 33/48757* (2013.01); *G01N 33/66* (2013.01)

(58) Field of Classification Search
CPC .......................... G01N 33/48757; G01N 33/66
See application file for complete search history.

(56) References Cited

U.S. PATENT DOCUMENTS

| D440,312 S | 4/2001 | Bertrand |
|---|---|---|
| 8,394,343 B2 | 3/2013 | Chan |
| D731,658 S | 6/2015 | Maentausta |
| 9,204,829 B2 | 12/2015 | Prais |
| 9,383,333 B2 | 7/2016 | Reynolds |
| 9,678,057 B2 | 6/2017 | Bilton |
| 2003/0191415 A1 | 10/2003 | Moerman |
| 2012/0302918 A1 | 11/2012 | Dietz |
| 2012/0330189 A1 | 12/2012 | Shaanan |
| 2015/0160186 A1 | 6/2015 | Garner-Richards |

FOREIGN PATENT DOCUMENTS

EP 1530722 3/2017

*Primary Examiner* — Christopher Adam Hixson
(74) *Attorney, Agent, or Firm* — Kyle A. Fletcher, Esq.

(57) ABSTRACT

The glucose testing device with test strip dispenser is a blood glucose testing device. The blood glucose testing device tests for the concentration of the sugar known as glucose in the blood of a patient. The blood sample tested by the blood glucose testing device is presented to the blood glucose testing device on a sheeting known as a glucose test strip. The glucose testing device with test strip dispenser comprises a strip dispenser and the blood glucose testing device. The strip dispenser attaches to the blood glucose testing device. The strip dispenser is a refillable storage device that stores a plurality of glucose test strips.

20 Claims, 6 Drawing Sheets

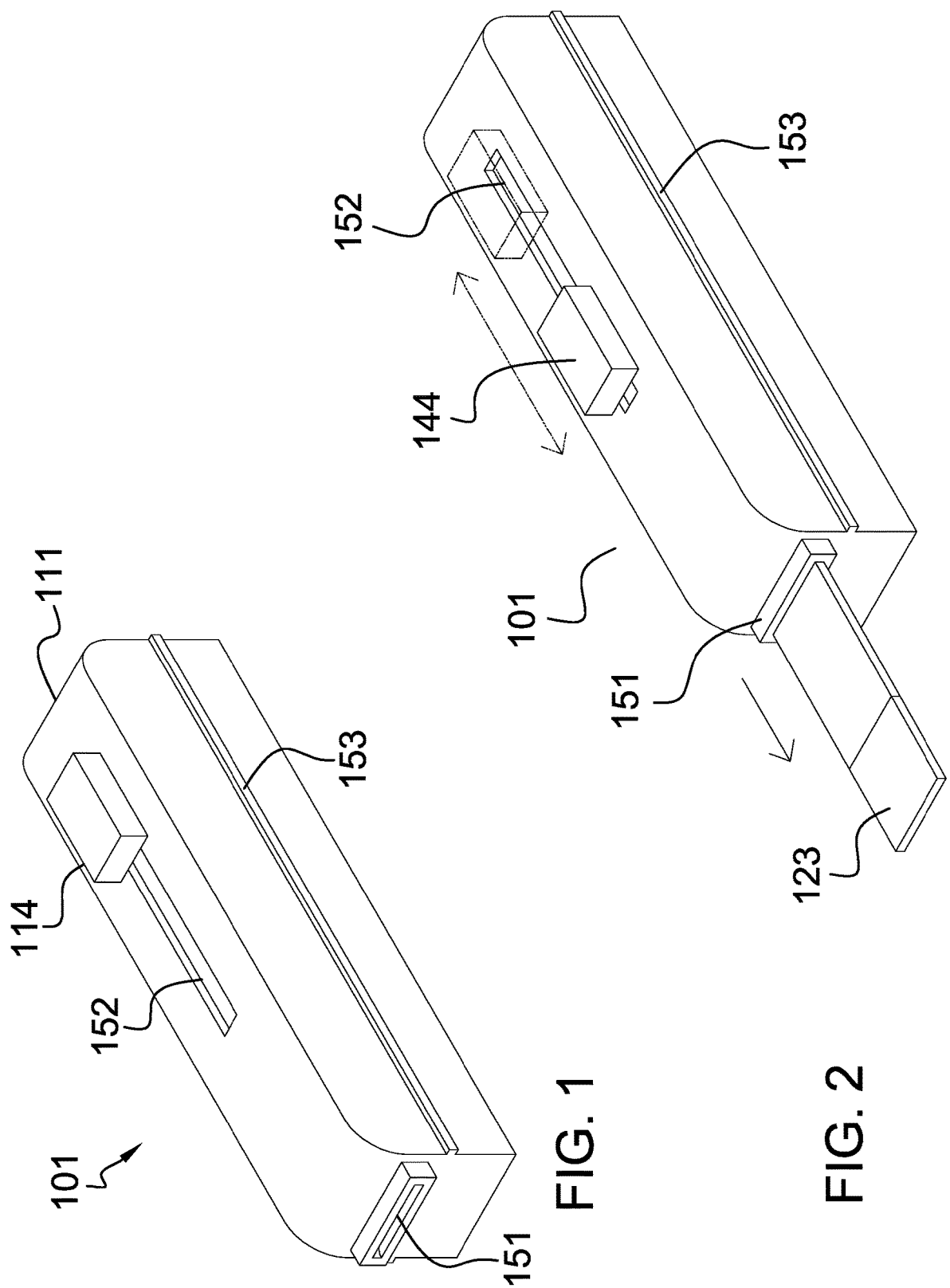

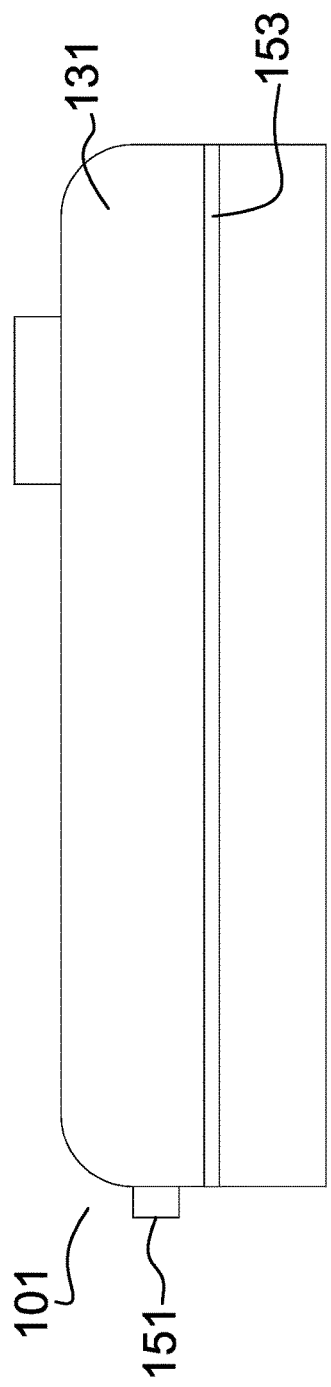
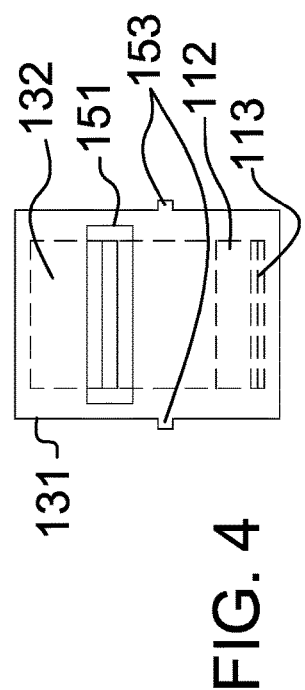
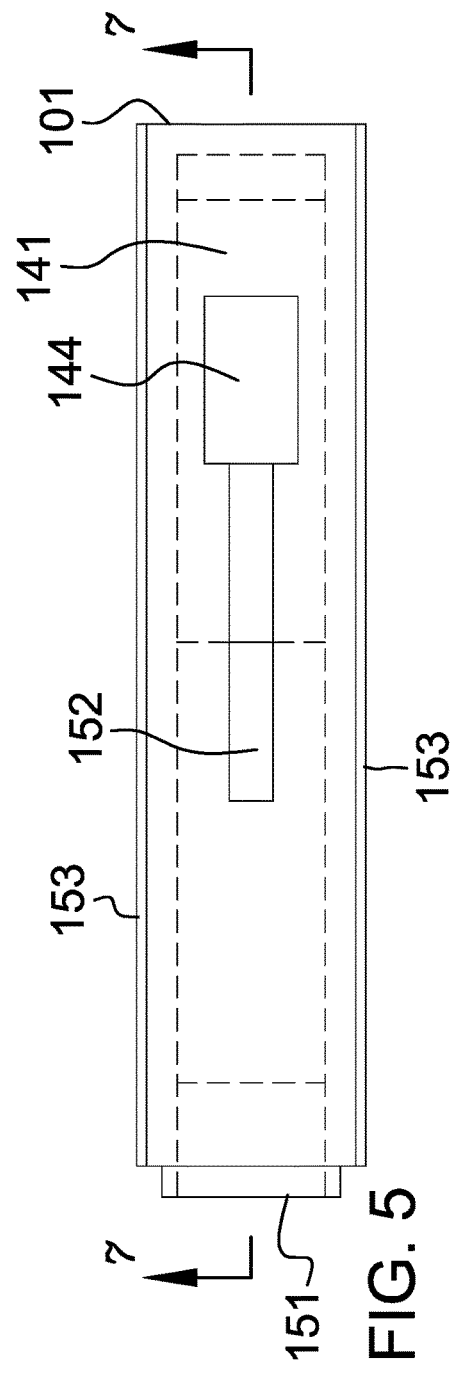
FIG. 3
FIG. 4
FIG. 5

GLUCOSE TESTING DEVICE WITH TEST STRIP DISPENSER

CROSS REFERENCES TO RELATED APPLICATIONS

Not Applicable

STATEMENT REGARDING FEDERALLY SPONSORED RESEARCH

Not Applicable

REFERENCE TO APPENDIX

Not Applicable

BACKGROUND OF THE INVENTION

Field of the Invention

The present invention relates to the field of physics including investigating and analyzing biological materials by determining their chemical and physical properties, more specifically, a detail of handling a testing element in the form of a test element dispensed from a stack. (G01N33/48757)

SUMMARY OF INVENTION

The glucose testing device with test strip dispenser is a blood glucose testing device. The blood glucose testing device tests for the concentration of the sugar known as glucose in the blood of a patient. The blood sample tested by the blood glucose testing device is presented to the blood glucose testing device on a sheeting known as a glucose test strip. The glucose testing device with test strip dispenser comprises a strip dispenser and the blood glucose testing device. The strip dispenser attaches to the blood glucose testing device. The strip dispenser is a refillable storage device that stores a plurality of glucose test strips.

These together with additional objects, features and advantages of the glucose testing device with test strip dispenser will be readily apparent to those of ordinary skill in the art upon reading the following detailed description of the presently preferred, but nonetheless illustrative, embodiments when taken in conjunction with the accompanying drawings.

In this respect, before explaining the current embodiments of the glucose testing device with test strip dispenser in detail, it is to be understood that the glucose testing device with test strip dispenser is not limited in its applications to the details of construction and arrangements of the components set forth in the following description or illustration. Those skilled in the art will appreciate that the concept of this disclosure may be readily utilized as a basis for the design of other structures, methods, and systems for carrying out the several purposes of the glucose testing device with test strip dispenser.

It is therefore important that the claims be regarded as including such equivalent construction insofar as they do not depart from the spirit and scope of the glucose testing device with test strip dispenser. It is also to be understood that the phraseology and terminology employed herein are for purposes of description and should not be regarded as limiting.

BRIEF DESCRIPTION OF DRAWINGS

The accompanying drawings, which are included to provide a further understanding of the invention are incorporated in and constitute a part of this specification, illustrate an embodiment of the invention and together with the description serve to explain the principles of the invention. They are meant to be exemplary illustrations provided to enable persons skilled in the art to practice the disclosure and are not intended to limit the scope of the appended claims.

FIG. 1 is a perspective view of an embodiment of the disclosure.

FIG. 2 is an in-use view of an embodiment of the disclosure.

FIG. 3 is a side view of an embodiment of the disclosure.

FIG. 4 is a front view of an embodiment of the disclosure.

FIG. 5 is a top view of an embodiment of the disclosure.

DETAILED DESCRIPTION OF THE EMBODIMENT

The following detailed description is merely exemplary in nature and is not intended to limit the described embodiments of the application and uses of the described embodiments. As used herein, the word "exemplary" or "illustrative" means "serving as an example, instance, or illustration." Any implementation described herein as "exemplary" or "illustrative" is not necessarily to be construed as preferred or advantageous over other implementations. All of the implementations described below are exemplary implementations provided to enable persons skilled in the art to practice the disclosure and are not intended to limit the scope of the appended claims. Furthermore, there is no intention to be bound by any expressed or implied theory presented in the preceding technical field, background, brief summary or the following detailed description.

Figure 6:
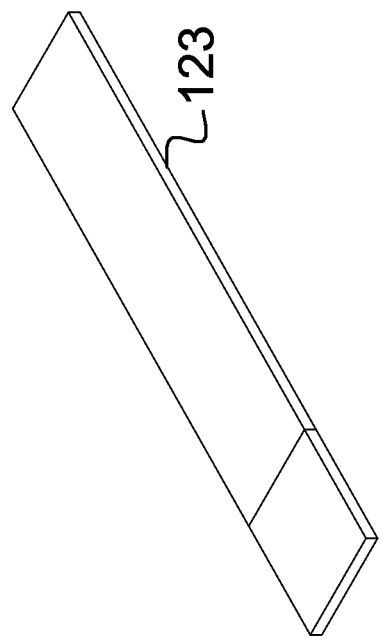
FIG. 6 is a detail view of an embodiment of the disclosure.
Figure 7:
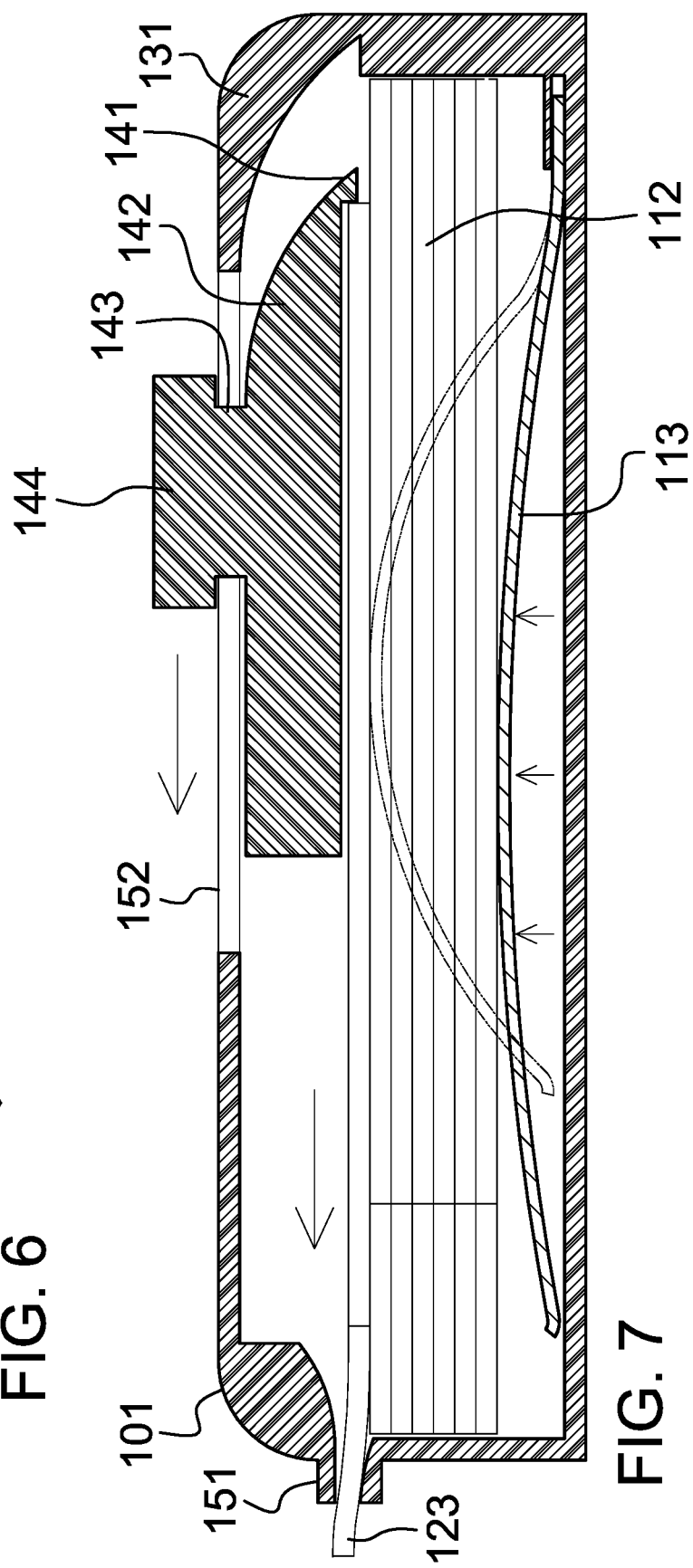
FIG. 7 is a cross-sectional view of an embodiment of the disclosure across 7-7 as shown in FIG. 5.
Figure 8:
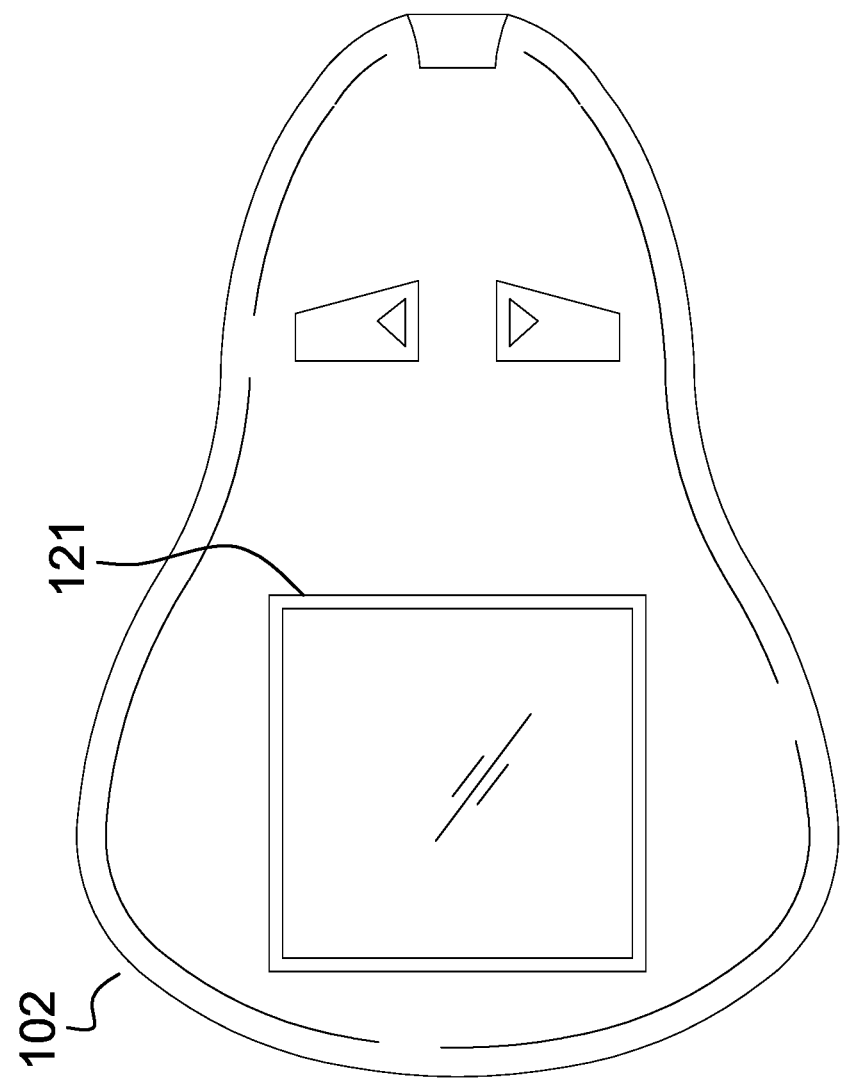
FIG. 8 is an in-use view of an embodiment of the disclosure.
Figure 9:
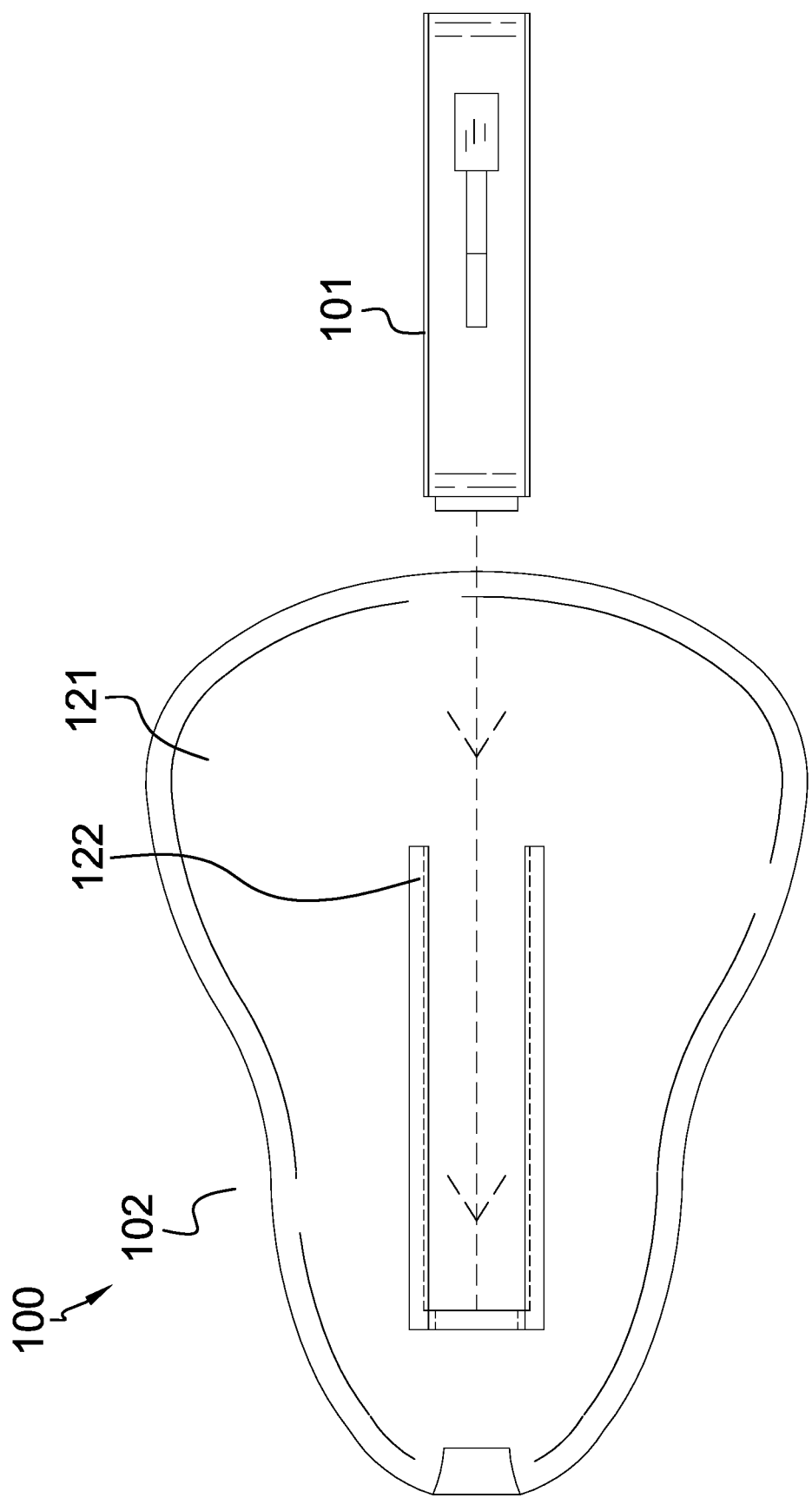
FIG. 9 is an in-use view of an embodiment of the disclosure.
Figure 10:
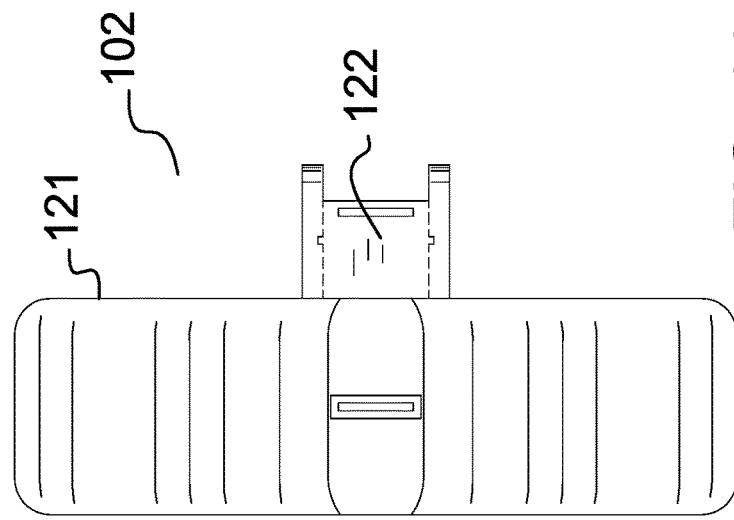
FIG. 10 is an in-use view of an embodiment of the disclosure.
Figure 11:
FIG. 11 is an in-use view of an embodiment of the disclosure.
Figure 12:
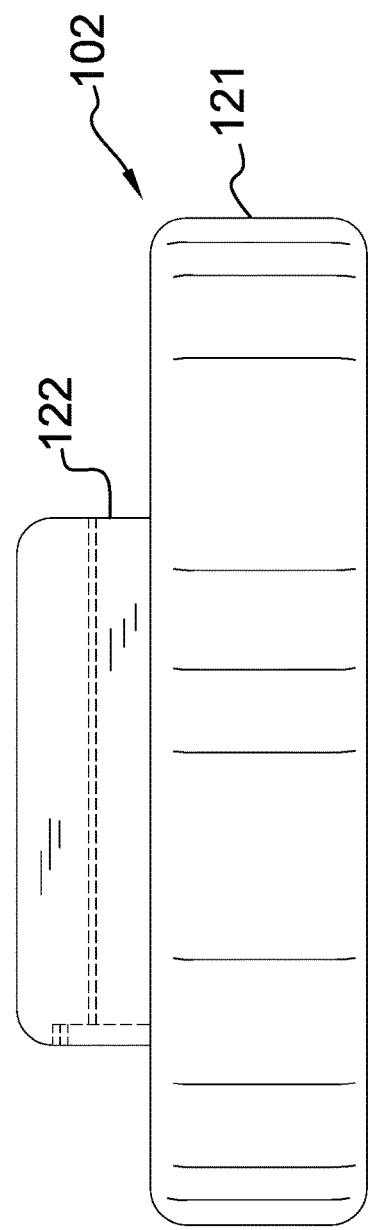
FIG. 12 is an in-use view of an embodiment of the disclosure.

Detailed reference will now be made to one or more potential embodiments of the disclosure, which are illustrated in FIGS. 1 through 12.

The glucose testing device with test strip dispenser 100 (hereinafter invention) is a blood glucose testing device 102. The blood glucose testing device 102 tests for the concentration of the sugar known as glucose in the blood of a patient. The blood sample tested by the blood glucose testing device 102 is presented to the blood glucose testing device 102 on a sheeting known as a glucose test strip 123. The invention 100 comprises a strip dispenser 101 and the blood glucose testing device 102. The strip dispenser 101 attaches to the blood glucose testing device 102. The strip dispenser 101 is a refillable storage device that stores a plurality of glucose test strips 123.

The blood glucose testing device 102 is an electric device. The blood glucose testing device 102 receives a sample of blood from the patient. The blood glucose testing device 102 measures the concentration of glucose in the blood of the patient. The blood glucose testing device 102 comprises a master device 121, a strip dispenser 101 mount 122, and a glucose test strip 123.

The master device 121 is an electric device. The master device 121 receives a sample of blood from the patient. The master device 121 analyzes the received blood sample to determine the concentration of glucose in the blood of the patient. The master device 121 displays the concentration of glucose in the blood of the patient.

The strip dispenser 101 mount 122 is a mechanical structure. The strip dispenser 101 mount 122 attaches the strip dispenser 101 to the exterior surface of the master device 121 such that the glucose test strip 123 can be dispensed directly from the strip dispenser 101 at the master device 121.

The glucose test strip 123 is a sheeting. The glucose test strip 123 receives a sample of blood from the patient and transports the blood sample into the master device 121 for analysis. The master device 121 and the glucose test strip 123 are well-known and documented in the medical arts.

The strip dispenser 101 is a containment structure. The strip dispenser 101 is a roughly rectangular block prism structure. The strip dispenser 101 is a hollow structure. The strip dispenser 101 contains a glucose test strip 123 stack 112. The strip dispenser 101 forms a mechanism that dispenses an individual glucose test strip 123 from the glucose test strip 123 stack 112. The strip dispenser 101 attaches to the exterior surface of the blood glucose testing device 102. The strip dispenser 101 comprises a housing 111, a glucose test strip 123 stack 112, a stack spring 113, and a lever 114. The housing 111 contains the glucose test strip 123 stack 112 and the stack spring 113. The lever 114 attaches to the housing 111.

The housing 111 is a rigid casing. The housing 111 has the primary shape of a rectangular block prism structure. The housing 111 contains the glucose test strip 123 stack 112. The housing 111 is formed with all apertures and form factors necessary to allow the housing 111 to accommodate the use and operation of the invention 100. Methods to form a housing 111 suitable for the purposes described in this disclosure are well-known and documented in the mechanical arts. The housing 111 comprises a shell 131 and a storage cavity 132.

The storage cavity 132 forms the hollow interior of the housing 111 that stores the glucose test strip 123 stack 112.

The shell 131 is a rigid structure. The shell 131 contains the glucose test strip 123 stack 112, the stack spring 113, and the lever 114. The shell 131 is formed with all apertures and form factors necessary to allow the shell 131 to accommodate the use and operation of the glucose test strip 123 stack 112, the stack spring 113, and the lever 114. Methods to form a shell suitable for the purposes described in this disclosure are well-known and documented in the mechanical arts. The shell 131 further comprises a discharge slot 151, a lever slot 152, and a plurality of mounting tracks 153.

The discharge slot 151 is an aperture that is formed through the exterior surface of the shell 131. The discharge slot 151 is positioned such that the glucose test strip 123 is discharged from the shell 131 through the discharge slot 151.

The lever slot 152 is an aperture that is formed through the exterior surface of the shell 131. The lever slot 152 is sized such that the extension structure 143 of the lever 114 will fit through the lever slot 152. The lever slot 152 is positioned such that the motion of the grip 144 moves the foot appropriately within the shell 131.

Each of the plurality of mounting tracks 153 is a rail. Each of the plurality of mounting tracks 153 mounts on the exterior surface of the shell 131. Each of the plurality of mounting tracks 153 fits into a channel formed within the strip dispenser 101 mount 122 such that the plurality of mounting tracks 153 removably attaches the strip dispenser 101 to the strip dispenser 101 mount 122. The use of mounting tracks in the manner described above are well-known and documented in the mechanical arts.

The glucose test strip 123 stack 112 comprises a plurality of glucose test strips 123. The centers of each of the plurality of glucose test strips 123 are aligned to form the glucose test strip 123 stack 112. Each glucose test strip 123 is dispensed individually from the glucose test strip 123 stack 112 by the lever 114 of the strip dispenser 101.

The stack spring 113 is a flat spring. The glucose test strip 123 stack 112 rests on the stack spring 113 such that the stack spring 113 is deformed beneath the stack spring 113. As each individual glucose test strip 123 is dispensed from the strip dispenser 101, the stack spring 113 further returns to its relaxed shape such that the remaining glucose test strip 123 that is distal from the stack spring 113 moves into a position relative to the lever 114 such that the distal glucose test strip 123 becomes the next glucose test strip 123 to be dispensed.

The stack spring 113 is a plate-shaped flat spring that is attached to the interior surface of the housing 111. The stack spring 113 acts as a spring. Specifically, when a force is applied perpendicularly to the surface of the stack spring 113, the elasticity of the stack spring 113 creates a rotational torque that opposes the displacement created by rotating the stack spring 113. This rotational torque places a strain on the stack spring 113 such that the force of the strain is in the direction that returns the stack spring 113 to its relaxed shape. When the glucose test strip 123 stack 112 is inserted between the stack spring 113 and the lever 114, this spring-like action produces a clamping force that holds the glucose test strip 123 stack 112 securely in position against the lever 114.

The use of a spring to perform the function of the stack spring 113 is well-known and documented in the mechanical arts.

The lever 114 is a mechanical apparatus. The lever 114 physically removes the glucose test strip 123 that is distal from the stack spring 113 from the glucose test strip 123 stack 112 and discharges the glucose test strip 123 from the housing 111. The lever 114 is a sliding structure that slides an individual glucose test strip 123 from the glucose test strip 123 stack 112. The lever 114 comprises a foot 141, a catch ledge 142, an extension structure 143, and a grip 144.

The foot 141 is a roughly rectangular block structure. The foot 141 is positioned against the glucose test strip 123 selected from the glucose test strip 123 stack 112 that is distal from the stack spring 113 and the interior surface of the storage cavity 132 of the shell 131. The foot 141 mounts within the shell 131 such that the foot 141 slides within the interior space of the shell 131.

The catch ledge 142 is a ledge that attaches to the foot 141. The catch ledge 142 projects away from the foot 141 in the direction towards the stack spring 113. The catch ledge 142 is positioned along the edge of the individual glucose test strip 123 of the glucose test strip 123 stack 112 that is proximal to the foot 141. The catch ledge 142 is positioned along the edge of the individual glucose test strip 123 of the glucose test strip 123 stack 112 such that the catch ledge 142 will catch and push the glucose test strip 123 towards and through the discharge slot 151 of the shell 131. The foot 141 drives the motion of the catch ledge 142 as the foot 141 slides within the interior space of the shell 131.

The extension structure 143 is an extension structure 143 that extends the reach between the surface of the foot 141 that is distal from the catch ledge 142 and the grip 144. The extension structure 143 is sized such that the extension structure 143 will fit through the lever slot 152 of the shell 131. The extension structure 143 is sized such that the extension structure 143 will freely slide within the lever slot of the shell 131. The extension structure 143 attaches the grip 144 to the foot 141 such that the grip 144 is accessible from the exterior of the shell 131.

The grip 144 is a prism-shaped structure. The grip 144 forms a control point that allows for the manipulation of the foot 141 within the shell 131. A user can simply push the grip 144 in order to move the foot 141 within the shell 131 in order to discharge the glucose test strip 123 from the strip dispenser 101.

The following definitions were used in this disclosure:

Carbohydrate: As used in this disclosure, a carbohydrate refers to a polymer chain formed from sugar molecules. The chemical formula of carbohydrates takes the general form of $C_x(H2O)_x$ where x is a positive integer. Carbohydrates are often referred to as a starch.

Carbon: As used in this disclosure, carbon (CAS 7440-44-0) refers to the element with atomic number 6 in the periodic table. The chemical abbreviation for carbon is C.

Channel: As used in this disclosure, a channel is a negative space used to guide the motion of an object.

Extension Structure: As used in this disclosure, an extension structure is an inert physical structure that is used to extend or bridge the reach between any two objects.

Exterior: As used in this disclosure, the exterior is used as a relational term that implies that an object is not contained within the boundary of a structure or a space.

Flat Spring: As used in this disclosure, a flat spring is a device designed to store and release mechanical energy that is made of a flat or conical piece of material.

Form Factor: As used in this disclosure, the term form factor refers to the size and shape of an object.

Housing: As used in this disclosure, a housing is a rigid structure that encloses and protects one or more devices.

Interior: As used in this disclosure, the interior is used as a relational term that implies that an object is contained within the boundary of a structure or a space.

Not Significantly Different: As used in this disclosure, the term not significantly different compares a specified property of a first object to the corresponding property of a reference object (reference property). The specified property is considered to be not significantly different from the reference property when the absolute value of the difference between the specified property and the reference property is less than 10.0% of the reference property value. A negligible difference is considered to be not significantly different.

Patient: As used in this disclosure, a patient is a person who is designated to receive a medical treatment, therapy or service. The term patient may be extended to an animal when used within the context of the animal receiving veterinary treatment or services.

Primary Shape: As used in this disclosure, the primary shape refers to a description of the overall geometric shape of an object that is assembled from multiple components.

Prism: As used in this disclosure, a prism is a three-dimensional geometric structure wherein: 1) the form factor of two faces of the prism are congruent; and, 2) the two congruent faces are parallel to each other. The two congruent faces are also commonly referred to as the ends of the prism. The surfaces that connect the two congruent faces are called the lateral faces. In this disclosure, when further description is required a prism will be named for the geometric or descriptive name of the form factor of the two congruent faces. If the form factor of the two corresponding faces has no clearly established or well-known geometric or descriptive name, the term irregular prism will be used. The center axis of a prism is defined as a line that joins the center point of the first congruent face of the prism to the center point of the second corresponding congruent face of the prism. The center axis of a prism is otherwise analogous to the center axis of a cylinder. A prism wherein the ends are circles is commonly referred to as a cylinder.

Rail: As used in this disclosure, a rail is a continuous structure that forms a track that is used to guide the motion of an object.

Reach: As used in this disclosure, reach refers to a span of distance between any two objects.

Rectangular Block: As used in this disclosure, a rectangular block refers to a three-dimensional prism structure comprising six rectangular surfaces (commonly called faces) formed at right angles. Within this disclosure, a rectangular block may further comprise rounded edges and corners.

Relaxed Shape: As used in this disclosure, a structure is considered to be in its relaxed state when no shear, strain, or torsional forces are being applied to the structure.

Roughly: As used in this disclosure, roughly refers to a comparison between two objects. Roughly means that the difference between one or more parameters of the two compared objects are not significantly different.

Rounded: A used in this disclosure, the term rounded refers to the replacement of an apex, vertex, or edge or brink of a structure with a (generally smooth) curvature wherein the concave portion of the curvature faces the interior or center of the structure.

Rounded Rectangle: A used in this disclosure, a rounded rectangle is a rectangle wherein one or more of the corner structures of the rectangle are replaced with a curvature wherein the concave portion of the curvature faces the center of the rounded rectangle.

Sheeting: As used in this disclosure, a sheeting is a material, such as a paper, textile, a plastic, or a metal foil, in the form of a thin flexible layer or layers.

Shell: As used in this disclosure, a shell is a structure that forms an outer covering intended to contain an object. Shells are often, but not necessarily, rigid or semi-rigid structures that are intended to protect the object contained within it.

Spring: As used in this disclosure, a spring is a device that is used to store mechanical energy. This mechanical energy will often be stored by: 1) deforming an elastomeric material that is used to make the device; 2) the application of a torque to a semi-rigid structure; or 3) a combination of the previous two items.

Stack: As used in this disclosure, a stack refers to a collection of disk-shaped objects that are stored such that the centers of each of the disk-shaped objects are aligned. The term stack typically implies that the aligned centers are vertically oriented.

Starch: As used in this disclosure, a starch is a carbohydrate formed from monomers of alpha-D-glucose (CAS 492-62-6) molecules.

Strip: As used in this disclosure, the term describes a long and narrow object of uniform thickness that appears thin relative to the length of the object. Strips are often rectangular in shape.

Sugar: As used in this disclosure, a sugar refers to a carbohydrate that readily dissolves in water. This disclosure assumes that the carbohydrate that forms the sugar contains 12 or fewer carbon atoms.

Track: As used in this disclosure, a track is a structural relationship between a first object and a second object that serves a purpose selected from the group consisting of: 1) fastening the second object to the first object; 2) controlling the path of motion of the first object relative to the second object in at least one dimension and in a maximum of two dimensions; or, 3) a combination of the first two elements of this group.

With respect to the above description, it is to be realized that the optimum dimensional relationship for the various components of the invention described above and in FIGS. 1 through 12 include variations in size, materials, shape, form, function, and manner of operation, assembly and use, are deemed readily apparent and obvious to one skilled in the art, and all equivalent relationships to those illustrated in the drawings and described in the specification are intended to be encompassed by the invention.

It shall be noted that those skilled in the art will readily recognize numerous adaptations and modifications which can be made to the various embodiments of the present invention which will result in an improved invention, yet all of which will fall within the spirit and scope of the present invention as defined in the following claims. Accordingly, the invention is to be limited only by the scope of the following claims and their equivalents.

What is claimed is:

1. A blood testing apparatus comprising
a strip dispenser and the blood glucose testing device;
wherein the strip dispenser attaches to the blood glucose testing device;
wherein the blood testing apparatus tests for the concentration of the sugar known as glucose in the blood of a patient;
wherein the blood sample tested by the blood glucose testing device is presented to the blood glucose testing device on a sheeting known as a glucose test strip;
wherein the strip dispenser is a refillable storage device that stores a plurality of glucose test strips.

2. The blood testing apparatus according to claim 1
wherein the blood glucose testing device is an electric device;
wherein the blood glucose testing device measures the concentration of glucose in the blood of the patient.

3. The blood testing apparatus according to claim 2
wherein the strip dispenser is a roughly rectangular block prism structure;
wherein the strip dispenser is a hollow structure;
wherein the strip dispenser contains a glucose test strip stack;
wherein the strip dispenser forms a mechanism that dispenses an individual glucose test strip from the glucose test strip stack.

4. The blood testing apparatus according to claim 3 wherein the strip dispenser attaches to the exterior surface of the blood glucose testing device.

5. The blood testing apparatus according to claim 4
wherein the blood glucose testing device comprises a master device, a strip dispenser mount, and the glucose test strip;
wherein the strip dispenser mount attaches the strip dispenser to the exterior surface of the master device such that the glucose test strip can be dispensed directly from the strip dispenser at the master device.

6. The blood testing apparatus according to claim 5
wherein the strip dispenser comprises a housing, a glucose test strip stack, a stack spring, and a lever;
wherein the housing contains the glucose test strip stack and the stack spring;
wherein the lever attaches to the housing.

7. The blood testing apparatus according to claim 6
wherein the master device is an electric device;
wherein the master device receives a sample of blood from the patient;
wherein the master device analyzes the received blood sample to determine the concentration of glucose in the blood of the patient;
wherein the master device displays the concentration of glucose in the blood of the patient.

8. The blood testing apparatus according to claim 7
wherein the strip dispenser mount is a mechanical structure;
wherein the glucose test strip is a sheeting;
wherein the glucose test strip receives a sample of blood from the patient and transports the blood sample into the master device for analysis.

9. The blood testing apparatus according to claim 8
wherein the housing is a rigid casing;
wherein the housing has the primary shape of a rectangular block prism structure.

10. The blood testing apparatus according to claim 9
wherein the housing comprises a shell and a storage cavity;
wherein the storage cavity forms the hollow interior of the housing that stores the glucose test strip stack.

11. The blood testing apparatus according to claim 10
wherein the shell is a rigid structure;
wherein the shell contains the glucose test strip stack, the stack spring, and the lever.

12. The blood testing apparatus according to claim 11
wherein the shell further comprises a discharge slot, a lever slot, and a plurality of mounting tracks;
wherein the discharge slot is an aperture that is formed through the exterior surface of the shell;
wherein the lever slot is an aperture that is formed through the exterior surface of the shell;
wherein each of the plurality of mounting tracks is a rail.

13. The blood testing apparatus according to claim 12
wherein the discharge slot is positioned such that the glucose test strip is discharged from the shell through the discharge slot;
wherein the lever slot is positioned such that the motion of the grip moves the foot appropriately within the shell;
wherein each of the plurality of mounting tracks mounts on the exterior surface of the shell.

14. The blood testing apparatus according to claim 13 wherein each of the plurality of mounting tracks fits into a channel formed within the strip dispenser mount such that the plurality of mounting tracks removably attaches the strip dispenser to the strip dispenser mount.

15. The blood testing apparatus according to claim 14
wherein the glucose test strip stack comprises a plurality of glucose test strips;
wherein the centers of each of the plurality of glucose test strips are aligned to form the glucose test strip stack;
wherein each glucose test strip is dispensed individually from the glucose test strip stack by the lever of the strip dispenser;
wherein the stack spring is a flat spring;

wherein the glucose test strip stack rests on the stack spring such that the stack spring is deformed beneath the stack spring;

wherein as each individual glucose test strip is dispensed from the strip dispenser, the stack spring further returns to its relaxed shape such that the remaining glucose test strip that is distal from the stack spring moves into a position relative to the lever such that the distal glucose test strip becomes the next glucose test strip to be dispensed;

wherein the stack spring is a plate-shaped flat spring that is attached to the interior surface of the housing.

16. The blood testing apparatus according to claim 15 wherein the lever is a mechanical apparatus;

wherein the lever physically removes the glucose test strip that is distal from the stack spring from the glucose test strip stack and discharges the glucose test strip from the housing;

wherein the lever is a sliding structure that slides an individual glucose test strip from the glucose test strip stack.

17. The blood testing apparatus according to claim 16 wherein the lever comprises a foot, a catch ledge, an extension structure, and a grip;

wherein the catch ledge is a ledge that attaches to the foot;

wherein the extension structure is an extension structure that extends the reach between the surface of the foot that is distal from the catch ledge and the grip.

18. The blood testing apparatus according to claim 17 wherein the foot is a roughly rectangular block structure;

wherein the foot is positioned against the glucose test strip selected from the glucose test strip stack that is distal from the stack spring and the interior surface of the storage cavity of the shell;

wherein the foot mounts within the shell such that the foot slides within the interior space of the shell.

19. The blood testing apparatus according to claim 18 wherein the catch ledge projects away from the foot in the direction towards the stack spring;

wherein the catch ledge is positioned along the edge of the individual glucose test strip of the glucose test strip stack that is proximal to the foot;

wherein the catch ledge is positioned along the edge of the individual glucose test strip of the glucose test strip stack such that the catch ledge will catch and push the glucose test strip towards and through the discharge slot of the shell;

wherein the foot drives the motion of the catch ledge as the foot slides within the interior space of the shell.

20. The blood testing apparatus according to claim 19 wherein the extension structure is sized such that the extension structure will fit through the lever slot of the shell;

wherein the extension structure is sized such that the extension structure will freely slide within the lever slot of the shell;

wherein the extension structure attaches the grip to the foot such that the grip is accessible from the exterior of the shell;

wherein the lever slot is sized such that the extension structure of the lever will fit through the lever slot;

wherein the grip is a prism-shaped structure;

wherein the grip forms a control point that allows for the manipulation of the foot within the shell.

\* \* \* \* \*